United States Patent [19]

Itoh

[11] Patent Number: 5,688,361

[45] Date of Patent: Nov. 18, 1997

[54] AUTOMATIC VESSEL SUPPLYING AND LABELING APPARATUS

[76] Inventor: Teruaki Itoh, 5-25, Kokaihonmachi, Kumamoto-shi, Kumamoto-ken 860, Japan

[21] Appl. No.: 652,670

[22] Filed: May 28, 1996

Related U.S. Application Data

[63] Continuation-in-part of Ser. No. 118,298, Sep. 9, 1993, abandoned.

[51] Int. Cl.$^6$ .................. B32B 31/00; B65C 9/40
[52] U.S. Cl. .................. 156/362; 156/352; 156/363; 156/542; 156/566; 156/DIG. 40; 209/523; 209/524
[58] Field of Search .................. 156/352, 362, 156/363, 540, 541, 542, 566, DIG. 44, DIG. 39, DIG. 40; 209/522, 523, 524

[56] References Cited

U.S. PATENT DOCUMENTS

| | | |
|---|---|---|
| 2,161,470 | 6/1939 | Holm .................. 156/481 |
| 3,553,041 | 1/1971 | Von Hofe .................. 156/378 |
| 3,653,176 | 4/1972 | Gess .................. 53/64 |
| 4,589,141 | 5/1986 | Christian et al. .................. 382/143 |
| 4,626,314 | 12/1986 | Wesley .................. 156/449 |
| 5,150,795 | 9/1992 | Nakayama et al. .................. 209/3.3 |
| 5,208,762 | 5/1993 | Charhut et al. .................. 364/478.04 |

FOREIGN PATENT DOCUMENTS

| | | |
|---|---|---|
| 0 510 615 A1 | 10/1992 | European Pat. Off. . |
| 59119266 | 7/1984 | Japan . |
| 3041365 | 2/1991 | Japan . |
| 4031235 | 2/1992 | Japan . |
| 4154534 | 5/1992 | Japan . |
| 5097133 | 4/1993 | Japan . |

*Primary Examiner*—David A. Simmons
*Assistant Examiner*—Paul M. Rivard
*Attorney, Agent, or Firm*—Nixon & Vanderhye

[57] ABSTRACT

An automatic vessel supplying and labeling apparatus takes out a desired vessel from racks, supplies it to a predetermined position, supplies a desired label, corresponding to the vessel, to the position, and applies the label to the vessel in the predetermined position. A judging unit checks the label information on the vessel, and judges whether the label is correctly applied to the vessel, and the vessel is sorted into one of two places, one place for collecting vessels with correctly applied labels and the other for collecting vessels with not correctly applied labels in accordance with the result of judgment. The label is applied to the vessel after a sensor detects the label supplied to the predetermined position.

8 Claims, 5 Drawing Sheets

AUTOMATIC VESSEL SUPPLYING AND LABELING APPARATUS

RELATED APPLICATIONS

This application is a continuation-in-part of application Ser. No. 08/118,298, filed Sep. 9, 1993, now abandoned, the disclosure of which is incorporated herein by reference.

TECHNICAL FIELD

The present invention relates to an automatic vessel supplying and labeling apparatus for automatically taking out a desired vessel from various vessels which are stored in accordance with a specific classification and automatically applying a corresponding label to the taken-out vessel.

BACKGROUND

The automatic vessel supplying and labeling apparatus as described above is used, for example to automatically take out a desired number of test tubes of desired sizes for use in desired tests from test tubes of various sizes, and to automatically apply labels, showing desired information necessary for the test, to the taken-out test tubes.

More specifically, the automatic vessel supplying and labeling apparatus is used to apply bar-code labels, showing desired information, to blood-collecting tubes automatically taken out from vessel classification and storage means.

For example in a hospital, when a patient is subjected to various blood tests, first, blood-collecting tubes of various sizes optimal for the tests are prepared. Each of the blood-collecting tubes label is applied for showing desired information such as the name of a patient, the date of blood collection, the medical department in charge, the name of a doctor in charge and the type of a blood test.

Then, blood is extracted from the patient into the blood-collecting tubes of various sizes in the proper amount. The blood-collecting tubes containing the blood are transported to a blood-test station inside or outside of the hospital. In the blood-test station, the blood-collecting tubes are respectively transferred to blood-test apparatuses or blood-test sections in accordance with the types of test and are subjected to the corresponding blood test. The results obtained by the blood-test apparatuses or sections are gathered after the tests and written on a blood test report and the report is transported to the medical department of the hospital in charge.

DISCLOSURE OF THE INVENTION

The above procedures other than the blood test have been simplified by automation using bar code labels. However, the aforementioned conventional automatic test tube supplying and labeling apparatuses used in hospitals frequently fail to apply labels to tubes, and demand has arisen for a more reliable apparatus for preparing blood-collecting tubes and applying labels to the tubes.

The present invention has been derived from the above situation and its object is to provide an automatic vessel supplying and labeling apparatus which can apply labels to vessels such as test tubes more reliably and sooner than the conventional apparatus, thereby improving the working efficiency.

To achieve the above object, according to the present invention, there is provided an automatic vessel supplying and labeling apparatus comprising:

vessel classification storage means for storing various vessels in accordance with a predetermined classification;

vessel take-out/supply means for taking out a desired vessel from the vessel classification storage means and for supplying the desired vessel to a vessel supply position;

label supplying means for preparing various labels on which information is displayed, and for supplying a desired label corresponding to the desired vessel in the various labels, to a label supply position separated from the vessel supply position;

label supply detection means for detecting the desired label at the label supply position;

label applying means for receiving the desired vessel from the vessel take-out/supply means at the vessel supply position, and for moving the received desired vessel between the vessel supply position and the label supply position through a waiting position which is positioned between the vessel supply position and the label supply position;

the label applying means moving the desired vessel from the vessel supply position to the waiting position when the label applying means receives the desired vessel from the vessel take-out/supply means and before the label supplying means supplies the desired label to the label supply position;

moving the desired vessel from the waiting position to the label supply position to apply the desired label on the desired vessel after the label supply detection means detects the desired label; and moving the desired vessel applied with the desired label from the label supply position to the vessel supply position and discharging the desired vessel applied with the desired label from the vessel supply position;

label application judging means for checking the information on the desired label applied on the desired vessel and judging whether the desired label is correctly applied on the desired vessel or not;

vessel sorting means for sorting the desired vessel on which the desired label has been applied by the label applying means into one of two places, the desired vessel on which the desired label has been applied correctly by the label applying means being sorted into one place, and the desired vessel on which the desired label has not been applied correctly by the label applying means being sorted into the other place; and correctly labeled vessel collecting means for collecting the desired vessel on which the desired label has been correctly applied by the label applying means and which is sorted by the vessel sorting means into the one place, wherein the label applying means includes at least three rollers arranged in parallel to each other and a rotational driving source for selectively rotating at least one of the rollers, two rollers in the at least three rollers being movable independent of the remaining roller between the vessel supply position and the label supply position through the waiting position, with the desired vessel being supported thereon, and the remaining roller being arranged at the label supply position to sandwich the desired vessel supported on the two rollers with the two rollers when the two rollers are arranged at the label supply position;

the rotational driving source rotates the at least one of the rollers when the two rollers are arranged at the label supply position and the desired vessel supported on the two rollers are sandwiched by the two rollers and the remaining roller so that the sandwiched desired vessel is rotated and the desired label supplied to the label supply position is applied on the rotated, sandwiched desired vessel;

one of the at least three rollers has two members separated coaxially from each other along a rotational axis of the one of the at least three rollers, and the label supply detection means is arranged at a position between the two members of the one of the at least three rollers.

With this structure, the label applying means applies the desired label on the desired vessel supplied to the vessel supply position by the vessel takeout/supply means at the label supply position, after the label supply detection means has detected that the desired label has been supplied to the label supply position. Therefore, the desired label can be applied to the desired vessel more reliably. Further, since the label supply detection means is arranged at a position between the two members of the one of the at least three rollers of the label apply means, the label supply detection means and the label apply means can be assembled compactly without preventing the desired label from being applied on the desired vessel more reliably.

And, since the two rollers in the at least three rollers of the label apply means are movable between the vessel supply position and the label supply position through the waiting position so that the desired vessel supported on the two rollers can be moved from the vessel supply position to the waiting position before the desired label is supplied to the label supply position, timing for applying the desired label on the desired vessel can be set more precisely and, thus, a possibility of failure of attachment of the desired label on the desired vessel can be more decreased.

In addition, the label application judging means checks the information on the desired label applied to the desired vessel and judges whether the desired label is correctly applied to the desired vessel, and thereafter the vessel sorting means sorts the desired vessel on which the desired label is applied into two places in accordance with the result of judgment of the label application judging means. Therefore, a desired vessel to which a desired label is erroneously applied is not supplied. Since the label supply detection means assembled with the label apply means decreases a possibility of discharge of the desired vessel on which the desired label has not been applied correctly by the label apply means from the label apply means to the label application judging means, waste of vessels and time needed to collect the predetermined number of the desired vessels on which the desired labels are applied correctly, can be reduced.

It is preferable that the correctly labeled vessel collecting means includes tray transfer means for supplying a tray to a place for collecting the desired vessel on which the desired label has been correctly applied by the label applying means and which is sorted by the vessel sorting means into the one place, and for selectively transferring out the tray from the place for collecting the desired vessel, and that the tray is detachably mounted on the tray transfer means.

With the tray transfer means and the tray as described above, it reduces human power needed for the automatic vessel supplying and labeling apparatus of the present invention.

In the automatic vessel supplying and labeling apparatus according to the present invention and constructed as described above, the vessels may be test tubes, and the label supplying means may include a label printer for printing information on the desired label.

Further, in the automatic vessel supplying and labeling apparatus according to the present invention and constructed as described above, at least a part of the information on the desired label is displayed by a bar code, and the label application judging means checks whether bar code data can be read from the bar code displayed on the desired label applied on the desired vessel or not, thereby judging whether the desired label is correctly applied to the desired vessel or not.

Moreover, it is preferable that when the label application judging means judges that the desired label is not correctly applied on the desired vessel, the vessel takeout/supply means takes out an additional vessel of the same type as that of the desired vessel from the vessel classification storage means and supplies the additional vessel to the vessel supply position, the label supplying means supplies an additional label, on which the same information as that displayed on the desired label is displayed, to the label supply position, and the label applying means applies the additional label to the additional vessel and discharges the additional label applied additional vessel to the label application judging means.

Furthermore, it is preferable that each of outer peripheral surfaces of the two rollers in the at least three rollers is coated with silicone, and also that an outer peripheral surface of the remaining roller in the at least three rollers is polished. The silicone coat prevents the desired label from adhering on the peripheral surfaces of the two rollers. And, the polished outer peripheral surface of the remaining roller strengthens adhesion of the desired label on the desired vessel.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and together with the general description given above and the detailed description of the preferred embodiment given below, serve to explain the principles of the invention.

BEST MODE FOR CARRYING OUT THE INVENTION

An embodiment of the present invention will be described with reference to the accompanying drawings.

Figure 1:
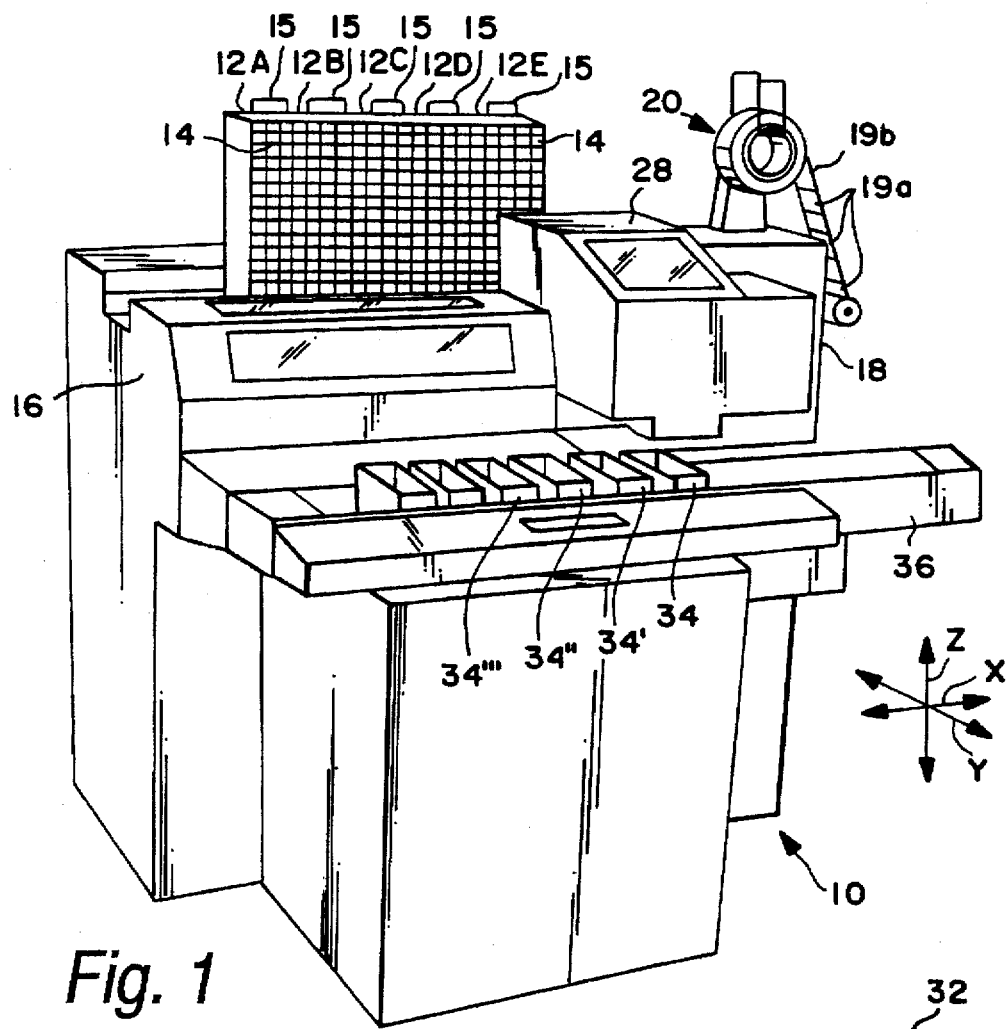
FIG. 1 is a perspective view schematically showing an appearance of an automatic vessel supplying and labeling apparatus according to an embodiment of the present invention.

FIG. 1 schematically shows the appearance of an automatic vessel supplying and labeling apparatus 10 according to an embodiment of the present invention. First, the schematic structure of the automatic vessel supplying and labeling apparatus 10 will be described mainly with reference to FIG. 1.

The automatic vessel supplying and labeling apparatus 10 comprises five racks 12A, 12B, 12C, 12D and 12E of a predetermined configuration, which serve as vessel classification storage means. The racks removably store a plurality of (five in this embodiment) types of vessels (blood-collecting test tubes) having different sizes, respectively.

Each of the racks 12A, 12B, 12C, 12D and 12E is a rectangle with the vertical sides longer than the horizontal sides, and includes a predetermined number of vessel storage chambers 14 arranged regularly in a matrix along an X axis (the horizontal direction in FIG. 1) and a Z axis (the vertical direction in FIG. 1).

Handles 15 are respectively attached to the upper surfaces of the racks 12A, 12B, 12C, 12D and 12E so that the racks can be handled easily.

Blood-collecting test tubes of a specific type (i.e., size) are manually inserted to the vessel storage chamber 14 of each of the racks 12A, 12B, 12C, 12D and 12E, while these racks are removed from the apparatus 10.

The automatic vessel supplying and labeling apparatus 10 comprises a vessel takeout/supply portion 16, which detachably holds, on its upper surface, the five racks 12A. 12B, 12C, 12D and 12E arranged adjacent to one another along the X axis. The vessel takeout/supply portion 16 takes out a desired vessel from the racks 12A, 12B, 12C, 12D and 12E in accordance with instructions input through an input device of a computer (not shown), and supplies it to a vessel supply position in the right side of the right end portion of the upper surface of the vessel takeout/supply portion 16.

The automatic vessel supplying and labeling apparatus 10 further comprises a label supplying portion 18 in the right side of the vessel supply position. The label supplying portion 18 detachably and rotatably holds a label roll 20 constituted by a rolled belt-like base sheet and a number of blank labels adhered thereon at regular intervals in its longitudinal direction. The label supplying portion serves as a label printer to print desired information, corresponding to the desired vessel taken out, on a blank label 19a adhered on the base sheet 19b in accordance with instructions input through the input device of the computer and supplies the printed label to a label supply position spaced above from the above-mentioned vessel supply position.

Figure 2:
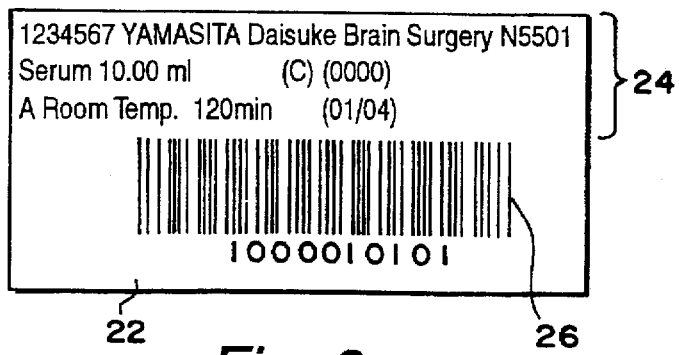
FIG. 2 is a plan view of a label on which desired information has been printed by a label supplying portion of the automatic vessel supplying and labeling apparatus shown in FIG. 1.

FIG. 2 shows an example of a printed label 22. The desired information includes items 24 such as the name of a patient, the date of blood collection, the medical department in charge, the name of a doctor in charge and the type of a blood test and a bar code 26 indicating some of these items.

Label supply detection means is arranged at the label supply position and a label applying portion is arranged to cover the label supply position and the vessel supply position between the vessel takeout/supply portion 16 and the label supplying portion 18 in FIG. 1. However, since the label supply detection means and the label applying portion are covered by a cover 28, they can not be seen in FIG. 1. The label supply detection means optically detects that the desired and printed label have been supplied to the label supply position by the label supplying means 20, and the label applying portion moves the desired vessel supplied to the vessel supply position by the vessel takeout/supply portion 16 from the vessel supply position to the label supply position through a waiting position to apply the desired and printed label on the desired vessel, after the label supply detection means detects that the desired and printed label have been supplied to the label supply position.

Figure 3:
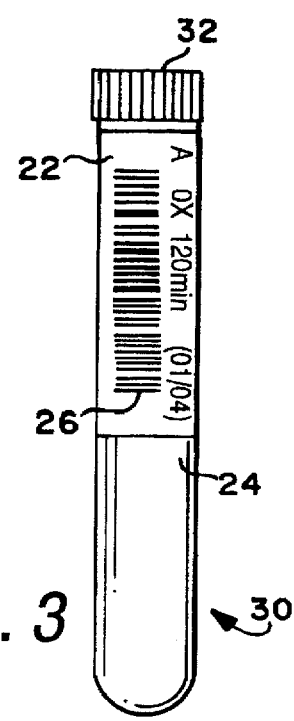
FIG. 3 is a front view of a blood-collecting test tube as an example of a desired vessel, on which the printed label shown in FIG. 2 has been applied by a label applying portion of the automatic vessel supplying and labeling apparatus shown in FIG. 1.

FIG. 3 shows a blood-collecting test tube 30 (a desired vessel) on which the desired and printed label 22 removed from the base sheet 19b of the label roll 20 is applied. The blood-collecting test tube 30 is vacuumed and thereafter sealed with an elastic synthetic resin film 32. Such a test tube has been widely used.

A bar-code reader and a vessel sorting portion are arranged in front of the vessel supply portion along a Y axis (in the back and fourth directions in FIG. 1) in the cover 28. The bar-code reader serves as a label application judging portion for judging whether the desired and printed label 22 is correctly applied to the desired blood-collecting test tube 30 based on the result that the reader reads the bar code 26 (FIG. 2) on the desired and printed label 22 attached to the desired blood-collecting test tube 30. The vessel sorting portion sorts the desired blood-collecting test tube 30, on which the desired and printed label is applied, into one of two portions, one portion of which is for collecting tubes on which labels are correctly applied, and the other portion of which is for collecting tubes on which labels are not correctly applied, in accordance with the result of judgment of the bar-code reader. Since the label application judging portion and the vessel sorting portion are also covered by the cover 28, they can not be seen in FIG. 1.

As shown in FIG. 1, a tray 34 for receiving the desired blood-collecting test tube 30, on which the desired and printed label 22 is correctly applied, is arranged in a position below the front end reign of the cover 28 to correspond to an opening for discharging vessels with correctly applied labels in one of the above mentioned two portions. The tray 34 is detachably supported in a tray receiver of a tray transfer portion 36 extending along the X axis (in the horizontal direction in FIG. 1). In this embodiment, the tray transfer portion 36 is constituted by a belt conveyor on which a number of tray receivers are arranged at predetermined intervals along the longitudinal direction thereof. As shown in FIG. 1, a number of empty trays (341, 3411, 34111, ...) are supported in the tray receivers in the left side of the tray 34.

The tray transfer portion 36 is operated by the computer (not shown) to move the tray 34 rightward in FIG. 1 by a predetermined distance, when the computer detects, on the basis of a signal supplied from the bar-code reader serving as the label application judging portion (not shown in FIG. 1), that the tray 34 has received a desired number of blood-collecting test tubes 30 of a desired type in accordance with the instructions input through the input device of the computer.

As the tray 34 is moved by the predetermined distance as described above by the tray transfer portion 36, the empty tray 341 in the left side of the tray 34 is moved to the aforementioned position below the opening for discharging vessels with correctly applied labels. In this state, the tray 341 waits for receiving a desired number of blood-collecting test tubes 30 of a desired type in accordance with the instructions input through the input device of the computer.

The following are detailed explanations, with reference to FIGS. 4, 5A, 5B and 6, of the vessel takeout/supply portion 16, the label supplying portion 18, the label supply detection means, the label applying portion, the label application judging portion and the vessel sorting portion of the automatic vessel supplying and labeling apparatus 10, which have been schematically described with reference to FIG. 1.

The vessel takeout/supply portion 16 comprises a vessel extruding unit 50 and a vessel receiving unit 52, which are arranged symmetrically in the back and fourth sides of the five racks 12A, 12B, 12C, 12D and 12E.

Figure 4:
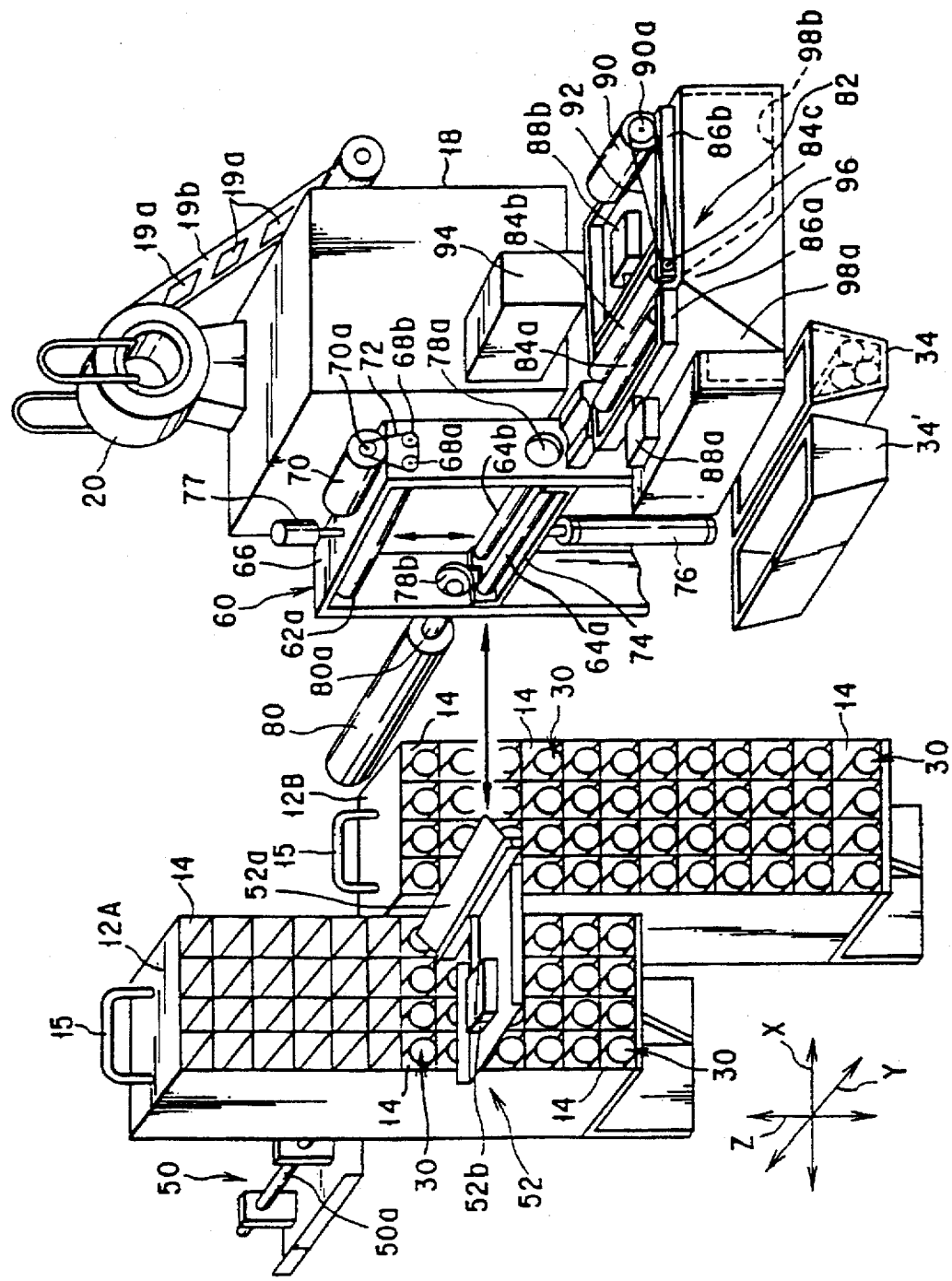
FIG. 4 is a perspective view schematically showing a main part of an inner structure of the automatic vessel supplying and labeling apparatus shown in FIG. 1.

The vessel takeout/supply portion 16 can simultaneously move the five racks 12A, 12B, 12C, 12D and 12E as one unit along the X axis, and the minimum pitch of the movement of the five racks is a pitch between the vessel storage chambers 14 along the X axis. It can also move the five racks 12A, 12B, 12C, 12D and 12D individually along the Z axis, and the minimum pitch of the movement of each is a pitch between the vessel storage chambers 14 along the Z axis. In FIG. 4, only two racks 12A and 12B are shown to make FIG. 4 simple.

Thus, the vessel takeout/supply portion 16 can quickly and accurately place one of the vessel storage chambers 14 for storing the blood-collecting test tubes 30 of one of the racks 12A, 12B, 12C, 12D and 12E, in accordance with a predetermined order, to a position between the vessel extruding unit 50 and the vessel receiving unit 52.

The vessel extruding unit 50 is constituted by an air cylinder/piston assembly, and extrudes a piston 50a forward, when the vessel storage chamber 14 storing a desired blood-collecting test tube 30 is placed in front thereof, in accordance with the instruction input through the input device of the computer. As a result, the desired blood-collection test tube 30 is extruded forward from the vessel storage chamber 14, and is slid onto a vessel receiving member 52a, having a substantially Y-shaped cross section, of the vessel receiving unit 52.

The entire structure of the vessel receiving unit 52 is freely movable along the front surfaces of the five racks 12A, 12B, 12C, 12D and 12E in the horizontal direction (along the X axis) between a position in front of the vessel extruding unit 50 and the aforementioned vessel supply position (the right end side of the vessel takeout/supply portion 16). As soon as the vessel receiving unit 52 receives the desired blood-collecting test tube 30 on the vessel receiving member 52a, it moves to the aforementioned vessel supply position.

As shown in FIG. 4, the vessel receiving member 52a of the vessel receiving unit 52 is rotatable between a vessel receiving position at which the V-shaped vessel receiving surface of the vessel receiving member 52a is directed upward and a vessel discharging position at which the V-shaped vessel receiving surface is directed rightward. The vessel receiving member 52a is rotated selectively between the two positions by an air cylinder/piston assembly 52b.

In this embodiment, when the vessel receiving unit 52 reaches the aforementioned vessel supply position, the vessel receiving member 52a is rotated by means of the air cylinder/piston assembly 52b from the vessel receiving position to the vessel discharging position, and the desired blood-collecting test tube 30 is discharged from the vessel receiving member 52a.

Thereafter, the vessel receiving member 52a is returned to the vessel receiving position shown in FIG. 4 by the air cylinder/piston assembly 52b, and then the vessel receiving unit 52 is returned from the aforementioned vessel supply position to the position in front of the vessel extruding unit 50, as shown in FIG. 4, and waits for reception of another blood-collecting test tube 30. In the meantime, the piston 50a of the vessel extruding unit 50 has been moved backward to an initial position.

Figure 5A:
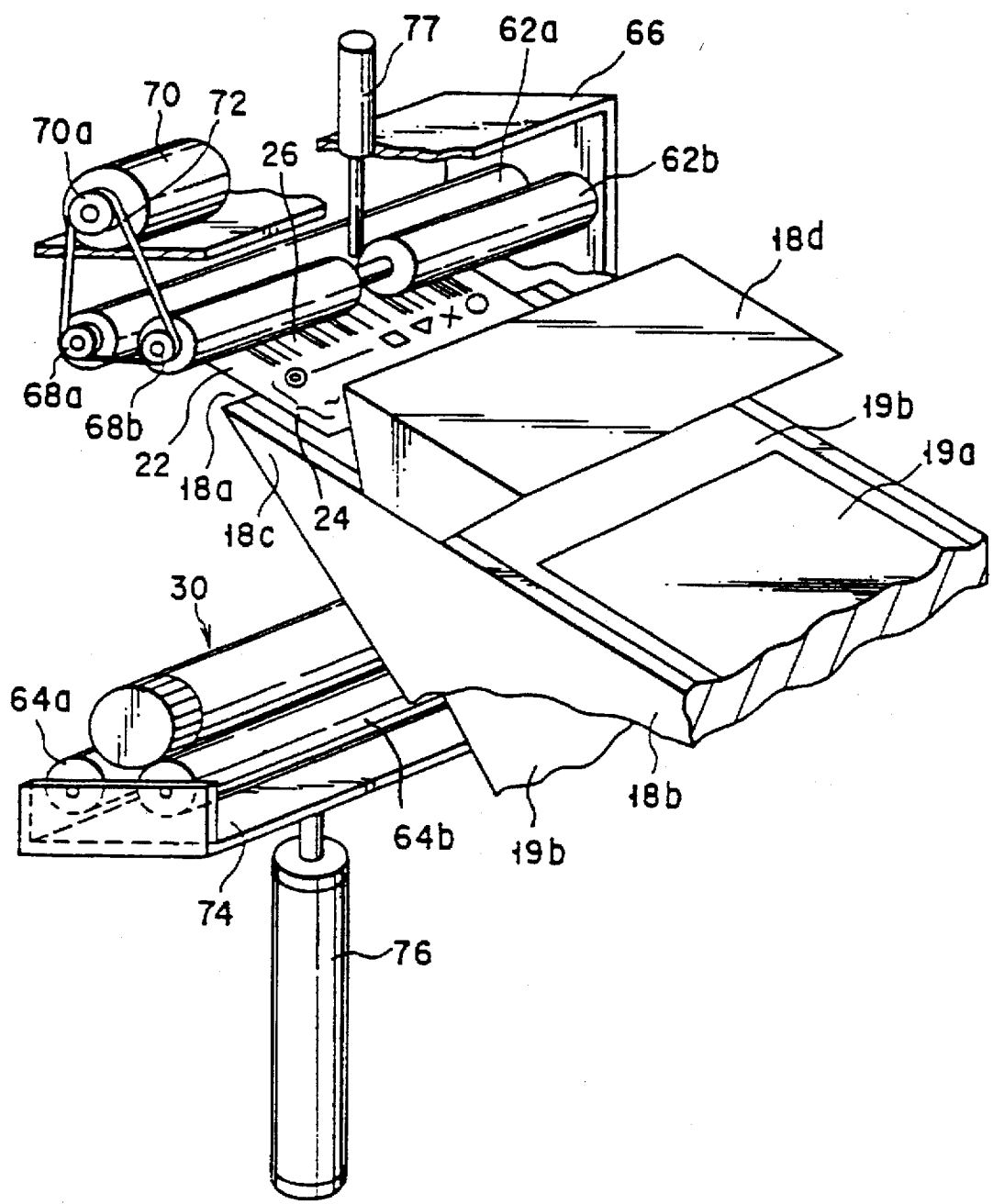
FIG. 5A is an enlarged perspective view schematically showing main parts of the label supplying portion, a label supply detection means and the label applying portion of the automatic vessel supplying and labeling apparatus shown in FIG. 1.

The label applying portion 60 comprises two pairs of upper rollers 62a and 62b and lower rollers 64a and 64b, as shown in FIGS. 4 and 5A.

The pair of upper rollers 62a and 62b are arranged in parallel with the vessel receiving member 52a of the vessel receiving unit 52, and are spaced apart from each other by a predetermined distance in the horizontal direction. The end portions of each of the rollers 62a and 62b are rotatably supported by a fixed supporting frame 66. Power transmission pulleys 68a and 68b are coaxially fixed to rotational shafts of the upper rollers 62a and 62b in the outside of the fixed supporting frame 66. A power transmission belt 72 is put on the power transmission pulleys 68a and 68b and a power transmission pulley 70a coaxially fixed to an output shaft of a motor 70 supported by the fixed supporting frame 66.

Similarly, the pair of lower rollers 64a and 64b are arranged in parallel with the vessel receiving member 52a of the vessel receiving unit 52, and are a predetermined distance spaced apart from each other in the horizontal direction. The end portions of each of the rollers 64a and 64b are rotatably supported with a movable supporting frame 74, which is movable upward and downward.

The movable supporting frame 74 is moved selectively between the vessel supply or lower position shown in FIGS. 4 and 5A and an upper position close to the label supply position or the pair of upper rollers 62a and 62b by means of an air cylinder/piston assembly 76.

The pair of rollers 64a and 64b on the movable supporting frame 74 at the vessel supply or lower position are horizontally adjacent to the vessel receiving member 52a of the vessel receiving unit 52, which has been transferred to the vessel discharging position where a desired blood-collecting test tube 30 is discharged. At this position, the pair of rollers 64a and 64b receive the desired blood-collecting test tube 30 discharged from the vessel receiving member 52a of the vessel receiving unit 52, as shown in FIG. 5A.

Referring to FIG. 5A, a label discharging port 18a of the label supplying portion 18 (FIG. 4) is located adjacently to the pair of upper rollers 62a and 62b. A label separating means 18c of a label guide 18b is provided in the label discharging port 18a. A printing means 18d is provided near to the label removing means 18c along the upper surface of the label guide 18b. The printing means 18d is constituted by, in this embodiment, a printing head using, for example, a thermal transfer printing ribbon (not shown).

The printing means 18b prints desired information corresponding to the desired blood-collecting test tube 30, in accordance with the instructions input through the input device of the computer (not shown), on a blank label 19a adhered to the base sheet 19b drawn out with a predetermined speed from the label roll 20 shown in FIG. 4 along the upper surface of the label guide 18b.

The base sheet 19b except for a portion corresponding to a rear end portion of the printed label 22 is separated from the printed label 22, on which the desired information has been printed by the printing means 18d, by means of the label separating means 18c arranged at the distal end of the label guide 18b. The label separating means 18c is constituted by forming the distal end to have an acute-angled edge. Since the base sheet 19b is bent downward at an acute angle by the label separating means 18c, the base sheet 19b is separated from the printed label 22. The separated portion of the printed label 22 is held in a state that it protrudes in the label supply position just under the pair of upper rollers 62a and 62b as shown in FIG. 5A.

In this embodiment, one of the upper rollers 62a and 62b located near to the label supplying portion 18 has two cylindrical members spaced coaxially from each other along a rotational axis of the one upper roller 62b. An optical label detection means 77 is provided on the fixed supporting frame 66 to project its lower end between the pair of upper rollers 62a and 62 and between the two cylindrical members of the one upper roller 62b. The optical label detection means 77 detects that the printed label 22 protrudes just under the pair of the upper roller 62a and 62b, or into the label supply position.

Figure 5B:
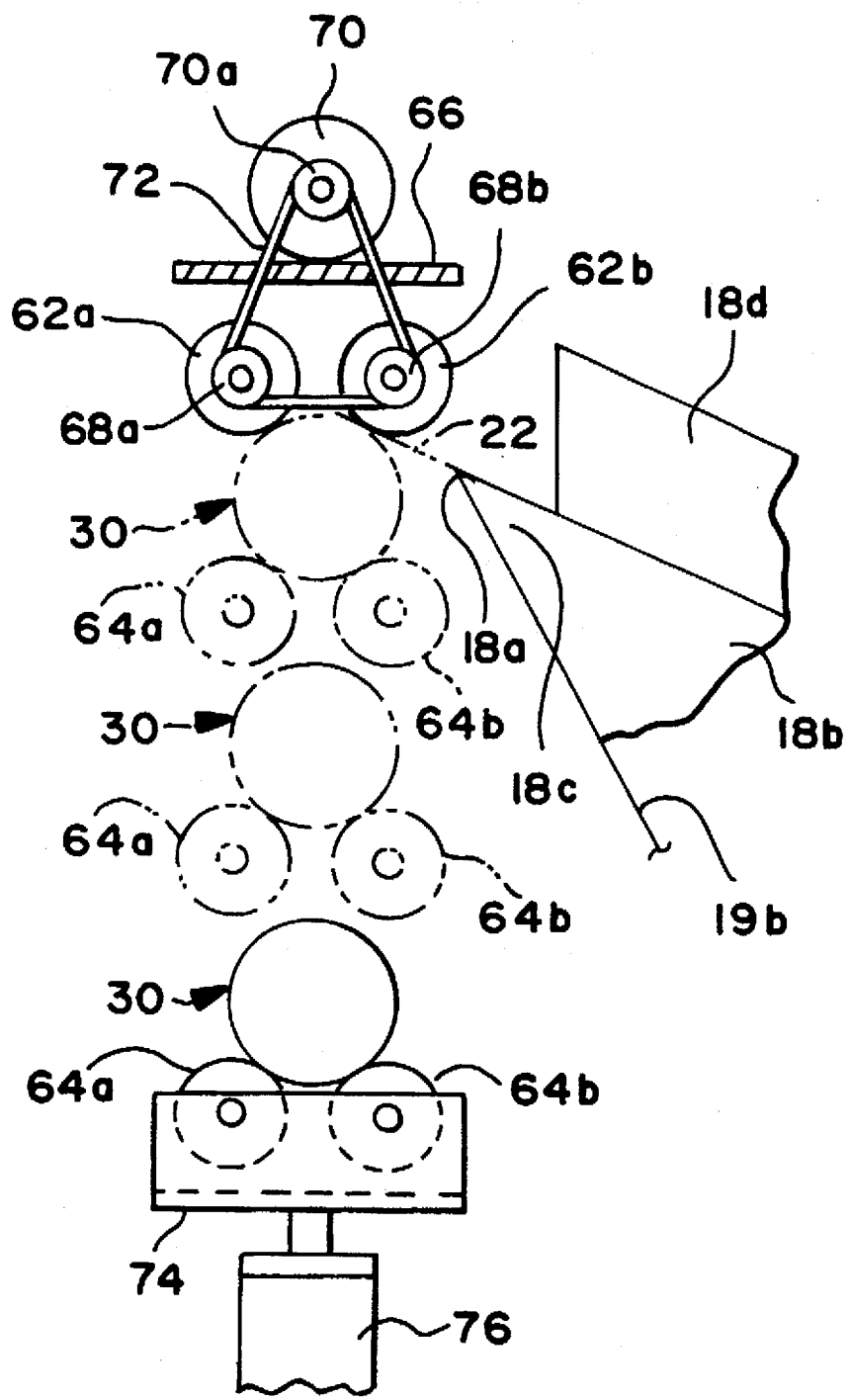
FIG. 5B is a side view schematically showing an operation of the label applying portion.

Until the optical label detection means 77 detects the printed label 22, the movable supporting frame 74 has been moved by the air cylinder/piston assembly 76 from the vessel supply or lower position to a waiting position between the lower vessel supply position and the upper label supply position. In FIG. 5B, the movable supporting frame 74 is shown by a solid line in the lower vessel supply position, and is shown by a two-dot chain line in each of the waiting position and the upper label supply position.

When the optical label detection means 77 detects the printed label 22, the movable supporting frame 74 is moved by the air cylinder/piston assembly 76 from the waiting position to the upper label supply position.

As a result, the desired blood-collecting test tube 30 on the pair of lower rollers 64a and 64b of the movable supporting frame 74 is pressed against the pair of upper rollers 62a and 62b. At this time, the protruding end portion of the printed label 22 protruding just under the upper rollers 62a and 62b is attached surely to the circumferential surface of the desired blood-collecting test tube 30.

In the label applying portion 60 for operating blood-collecting test tubes of various sizes, the air cylinder/piston assembly 76 of the movable supporting frame 74 stops the upward movement of the movable supporting frame 74 when it receive a certain resistance, in order to prevent the blood-collecting test tube 30 from being damaged by a pressure of the rollers 64a and 64b of the movable supporting frame 74.

When the upward movement of the movable supporting frame 74 is stopped, the motor 70 for driving the upper rollers 62a and 62b rotates the output shaft in a predetermined direction at a predetermined number of times, thereby rotating each of the upper rollers 62a and 62b in a predetermined direction at a predetermined times.

The printed label 22, the protruding end portion of which has been attached to the blood-collecting test tube 30, is entirely applied to the circumferential surface of the tube 30, while the tube 30 is being rotated in the predetermined direction by the upper rollers 62a and 62b. In this embodiment, each of the outer peripheral surfaces of the lower rollers 64a and 64b is coated with silicone, and each of the outer peripheral surfaces of the upper rollers 62a and 62b is polished. Such surface treatment prevents the printed label 22 from adhering on the each of the outer peripheral surfaces of the lower rollers 64a and 64b and causes the printed label 22 to be pressed more firmly on the peripheral surface of the tube 30 and to be attached more strongly to the peripheral surface of the tube 30.

After the predetermined number of rotation of the upper rollers 62a and 62b has been finished, the movable supporting frame 74 is returned to the vessel supply or lower position shown in FIGS. 4 and 5A by the air cylinder/piston assembly 76.

Through holes 78a and 78b are formed coaxially to one another in front and rear walls of the fixed supporting frame 66 at positions between the rollers 64a and 64b on the movable supporting frame 74 at the vessel supply or lower position. When the movable supporting frame 74 supporting the desired blood-collecting test tube 30 on which the printed label 22 has been attached is returned to the vessel supply or lower position, a piston 80a of an air cylinder/piston assembly 80 protrudes through the through hole 78b formed in the rear wall of the fixed supporting frame 66. The piston 80a thus protrudes the desired blood-collecting test tube 30 through the through hole 78a formed in the front wall of the fixed supporting frame 66. Thereafter, the piston 80a returns to its original position in the back side of the rear wall of the fixed supporting frame 66 through the rear through hole 78b.

The desired blood-collecting test tube 30 protruded forward from the label applying portion 60 slides onto a pair of rollers 84a and 84b of a vessel sorting portion 82.

The pair of rollers 84a and 84b extend in the direction along with the pair of rollers 64a and 64b of the label applying portion 60 are extended, and are spaced apart from each other by a predetermined distance in the horizontal direction. The both end portions of the rollers 84a, 84b are rotatably supported by a pair of horizontally movable supporting frames 86a and 86b which are movable independent of each other.

Each of the pair of horizontally-movable supporting frames 86a and 86b is movable horizontally along the x axis with respect to a fixed supporting frame (not shown). More specifically, the frames 86a and 86b are movable selectively between a close position shown in FIGS. 4 and 6 and a separate position at which either one of the movable frames is separated from the other by means of air cylinder/piston assemblies 88a and 88b respectively connected to the frames 86a and 86b.

A motor 90 is supported on one horizontally-movable supporting frame 86b (the right frame in FIG. 4). A power transmission pulley 90a is coaxially fixed to an output shaft of the motor 90, and a power transmission pulley 84c is coaxially fixed to a rotational shaft of the roller 84b on the horizontally-movable supporting frame 86b. A power transmission belt 92 is put on the pulleys 90a and 84c.

When the piston 80a of the air cylinder/piston assembly 80 of the label applying portion 60 begins to return behind the rear wall of the fixed supporting frame 66 after protruding the desired a blood-collection test tube 30 on which the printed label 22 is applied, the motor 90 on the horizontally-movable supporting frame 86b rotates the roller 84b in a predetermined direction, thereby rotating the desired blood-collecting test tube 30 on the pair of rollers 84a and 84b on the pair of horizontally-movable supporting frames 86a and 86b in the predetermined direction.

Figure 6:
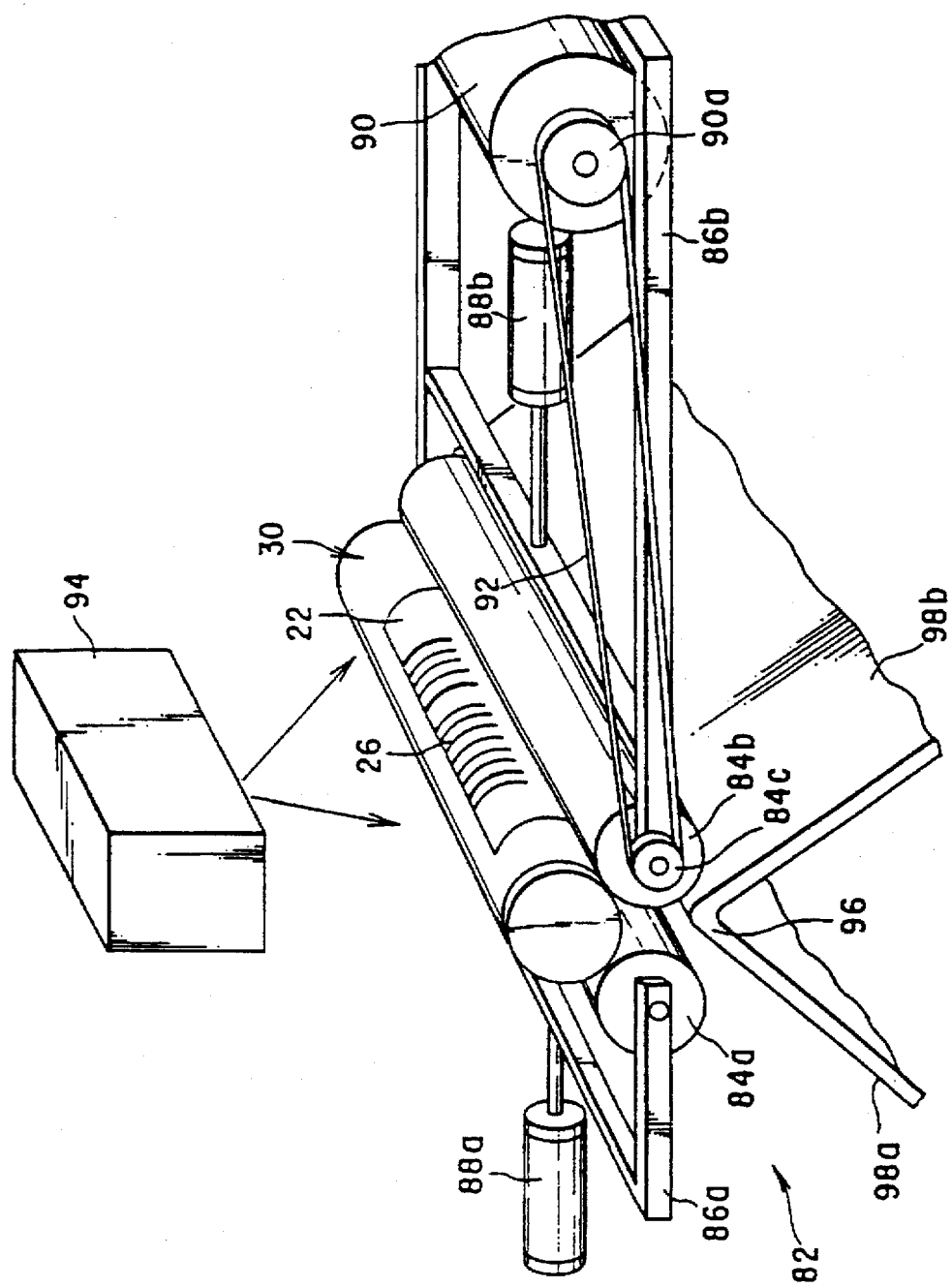
FIG. 6 is an enlarged perspective view schematically showing main parts of a label application judging portion and a vessel sorting portion of the automatic vessel supplying and labeling apparatus shown in FIG. 1.

A bar code reader 94, serving as a label application judging means, is arranged above a position where the pair of rollers 84a and 84b are close to each other as shown in FIGS. 4 and 6.

The bar code reader 94 reads bar code data from the bar code 26 on the printed label 22 attached to the desired blood-collection test tube 30 which is rotated as described above, and judges whether the read data coincides with the bar-coded items in accordance with the instructions input through the input device of the computer (not shown).

If the bar code reader 94 judges that the read data coincides with the aforementioned bar-coded items, the rotation of the motor 90 is stopped and the rotation of the blood-collecting test tube 30 on the pair of rollers 84a and 84b is stopped. Then, another horizontally-movable supporting frame 86a (the left frame in this embodiment) is moved leftward by the corresponding air cylinder/piston assembly 88a, thereby separating the roller 84a on the horizontally-movable supporting frame 86a from the roller 84b on the horizontally-movable supporting frame 86b.

As a result, the desired blood-collecting test tube 30 with the correctly applied printed label 22, which has been placed on the pair of rollers 84a and 84b, is dropped in the side of the roller 84a moved as described above.

A sorting member 96 is provided under the pair of rollers 84a and 84b in the close position as shown in FIGS. 4 and 6. The sorting member 96 has a substantially triangular cross-section and the ridge line of the sorting member 96 extends between the rollers 84a and 84b in the close position. With this structure, when the desired blood-collecting test tube 30 with the correctly applied printed label 22 drops in the side of the roller 84a, it falls down along one slope 98a (the left slope in this embodiment) of the sorting member 96 and is guided to the tray 34 positioned below the lower end of the slope 98a as shown in FIG. 4.

If the bar code reader 94 judges that the read data does not coincide with the aforementioned bar-coded items, this means failure in the printing operation by the printing means 18d (FIG. 5A) of the label supplying means 18 or failure in the label applying operation by the label applying portion 60. In this case, after the rotation of the motor 90 is stopped and the rotation of the blood-collecting test tube 30 on the pair of rollers 84a and 84b is stopped, the horizontally-movable supporting frame 86b (the right frame in this embodiment) is moved rightward by the corresponding air cylinder/piston assembly 88b, thereby separating the roller 84b on the horizontally-movable supporting frame 86b from the roller 84a on the horizontally-movable supporting frame 86a.

As a result, the blood-collecting test tube 30 with the badly applied or badly printed label 22 is dropped from the pair of rollers 84a and 84b into the side of the roller 84b moved as described above.

The desired blood-collecting test tube 30 dropped into the roller 84b side, falls down along the other slope 98b (the right slope in this embodiment) of the sorting member 96 and is guided to a failure test-tube collecting portion 98b positioned below the slope 98b as shown in FIG. 4.

When the bar code reader 94 detects the above described failure, the automatic vessel supplying and labeling apparatus 10 of this embodiment takes out another blood-collecting test tube 30 of the same type as the desired test tube 30 from the racks 12A, 12B, 12C, 12D and 12E, serving as the vessel classification storage means, by means of the vessel takeout/supply portion 16, and supplies it to the label applying portion 60 arranged in the right end side of the vessel takeout/supply portion 16. In the meantime, the label supplying portion 18 supplies an additional label, on which the same information as on the badly applied or badly printed label is printed, to the label applying portion 60, and the label applying portion 60 applies the additional label to the additional blood-collecting test tube 30. The blood-collecting test tube 30, on which the additional label is applied by the label applying portion 60, is supplied from the label applying portion 60 to a position under the bar code reader 94 serving as the label application judging means.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An automatic vessel supplying and labeling apparatus comprising:

vessel classification storage means for storing various vessels in accordance with a predetermined classification;

vessel take-out/supply means for taking out a desired vessel from the vessel classification storage means and for supplying the desired vessel to a vessel supply position;

label supplying means for preparing various labels on which information is displayed, and for supplying a desired label corresponding to the desired vessel in the various labels, to a label supply position separated from the vessel supply position;

label supply detection means for detecting the desired label at the label supply position;

label applying means for receiving the desired vessel from the vessel take-out/supply means at the vessel supply position, and for moving the received desired vessel between the vessel supply position and the label supply position through a waiting position which is positioned between the vessel supply position and the label supply position;

the label applying means moving the desired vessel from the vessel supply position to the waiting position when the label applying means receives the desired vessel from the vessel take-out/supply means and before the label supplying means supplies the desired label to the label supply position;

moving the desired vessel from the waiting position to the label supply position to apply the desired label on the desired vessel after the label supply detection means detects the desired label; and moving the desired vessel applied with the desired label from the label supply position to the vessel supply position and discharging the desired vessel applied with the desired label from the vessel supply position;

label application judging means for checking the information on the desired label applied on the desired vessel and judging whether the desired label is correctly applied on the desired vessel or not;

vessel sorting means for sorting the desired vessel on which the desired label has been applied by the label applying means into one of two places, the desired vessel on which the desired label has been applied correctly by the label applying means being sorted into one place, and the desired vessel on which the desired label has not been applied correctly by the label applying means being sorted into the other place; and correctly labeled vessel collecting means for collecting the desired vessel on which the desired label has been correctly applied by the label applying means and which is sorted by the vessel sorting means into the one place, wherein the label applying means includes at least three rollers arranged in parallel to each other and a rotational driving source for selectively rotating at least one of the rollers, two rollers in the at least three rollers being movable independent of the remaining roller between the vessel supply position and the label supply position through the waiting position, with the desired vessel being supported thereon, and the remaining roller being arranged at the label supply position to sandwich the desired vessel supported on the two rollers with the two rollers when the two rollers are arranged at the label supply position;

the rotational driving source rotates the at least one of the rollers when the two rollers are arranged at the label supply position and the desired vessel supported on the two rollers are sandwiched by the two rollers and the remaining roller so that the sandwiched desired vessel is rotated and the desired label supplied to the label supply position is applied on the rotated, sandwiched desired vessel;

one of the at least three rollers has two members separated coaxially from each other along a rotational axis of the one of the at least three rollers, and the label supply detection means is arranged at a position between the two members of the one of the at least three rollers.

2. An automatic vessel supplying and labeling apparatus according to claim 1, wherein the correctly labeled vessel collecting means includes tray transfer means for supplying a tray to a place for collecting the desired vessel on which the desired label has been correctly applied by the label applying means and which is sorted by the vessel sorting means into the one place, and for selectively transferring the tray from the place for collecting the desired vessel, and the tray is detachably mounted on the tray transfer means.

3. An automatic vessel supplying and labeling apparatus according to claim 1, wherein the vessels are test tubes.

4. An automatic vessel supplying and labeling apparatus according to claim 1, wherein the label supplying means includes a label printer for printing the information on the desired label.

5. An automatic vessel supplying and labeling apparatus according to claim 1, wherein at least a part of the information on the desired label is displayed by a bar code, and the label application judging means checks whether the bar code data can be read from the bar code displayed on the desired label applied on the desired vessel or not.

6. An automatic vessel supplying and labeling apparatus according to claim 1, wherein when the label application judging means judges that the desired label is not correctly applied on the desired vessel, the vessel take-out/supply means takes out an additional vessel of the same type as that of the desired vessel from the vessel classification storage means and applies the additional vessel to the vessel supply position, the label supplying means supplies an additional label on which the same information as that displayed on the desired label is displayed, to the label supply position, and the label applying means applies the additional label to the additional vessel and discharges the additional vessel applied with the additional label to the label application judging means.

7. An automatic vessel supplying and labeling apparatus according to claim 1, wherein each of outer peripheral surfaces of the two rollers in the at least three rollers is coated with silicone.

8. An automatic vessel supplying and labeling apparatus according to claim 1, wherein an outer peripheral surface of the remaining roller in the at least three rollers is polished.

* * * * *